United States Patent [19]

Barker et al.

[11] 4,042,369
[45] Aug. 16, 1977

[54] COMPOSITIONS AND METHODS OF COMBATTING WEEDS IN CROPS WITH 2,6-DIHALOBENZYL ETHER

[75] Inventors: Michael D. Barker, Maidstone; Eirlys R. Isaac, Sittingbourne; Peter Kirby, Maidstone; Graham C. Smith, Ramsgate, all of England

[73] Assignee: Shell Oil Company, Houston, Tex.

[21] Appl. No.: 572,535

[22] Filed: Apr. 28, 1975

Related U.S. Application Data

[62] Division of Ser. No. 481,723, June 21, 1974, Pat. No. 3,919,252.

[51] Int. Cl.² .................... A01N 9/28; C07D 317/16
[52] U.S. Cl. .......................................................... 71/88
[58] Field of Search ............................................. 71/88

[56] References Cited

U.S. PATENT DOCUMENTS

| 3,644,422 | 2/1972 | Mine et al. | 71/88 X |
| 3,753,678 | 8/1973 | Young et al. | 71/88 |
| 3,862,959 | 1/1975 | Kirby et al. | 71/88 X |
| 3,887,472 | 6/1975 | Kirby et al. | 71/88 X |
| 3,890,352 | 6/1975 | Isaac et al. | 71/88 X |
| 3,919,251 | 11/1975 | Isaac et al. | 71/88 X |

FOREIGN PATENT DOCUMENTS 1,293,546  10/1972  United Kingdom ................. 71/88

Primary Examiner—Joseph P. Brust

[57] ABSTRACT

Compounds of the formula

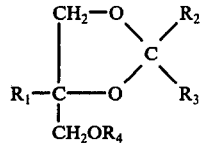

wherein $R_1$ is alkyl; $R_2$ is alkyl, aryl or aralkyl; $R_3$ is hydrogen or alkyl or $R_2$ and $R_3$ together is polymethylene; and $R_4$ is 2,6-dihalobenzyl are useful as herbicides.

8 Claims, No Drawings

COMPOSITIONS AND METHODS OF COMBATTING WEEDS IN CROPS WITH 2,6-DIHALOBENZYL ETHER

CROSS-REFERENCE TO RELATED APPLICATIONS

This application is a division Ser. No. 481,723 filed June 21, 1974, now U.S. Pat. No. 3,919,252 issued Nov. 11, 1975.

This invention relates to 2,6-dihalobenzyl ethers which are of interest as selective herbicides.

Accordingly the present invention provides 2,6-dihalobenzyl ethers having the following formula:-

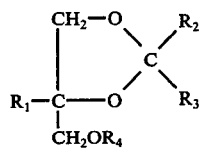

wherein $R_1$ represents an alkyl group; $R_2$ represents an alkyl, aryl or aralkyl group; $R_3$ represents a hydrogen atom or an alkyl group, or $R_2$ and $R_3$ together represent a polymethylene group; and $R_4$ represents a 2,6-dihalobenzyl group.

When $R_2$ represents an alkyl, aryl or aralkyl group these may be optionally substituted, for example by one or more halogen atoms or hydroxy groups. When $R_3$ represents an alkyl group this also may be optionally substituted, for example by one or more halogen atoms or hydroxy groups. The halogen atoms in the 2,6-dihalobenzyl group may be fluorine, chlorine, bromine or iodine or a mixture thereof, for example 2,6-dichlorobenzyl, 2-chloro-6-fluorobenzyl, or 2,6-difluorobenzyl.

The alkyl groups represented by $R_1$, $R_2$ and $R_3$ preferably contain 1 to 6 carbon atoms. The aryl and aralkyl groups preferably contain up to 8 carbon atoms and the polymethylene group up to 6 carbon atoms.

The benzyl ethers according to the invention which have shown considerable selective herbicidal activity are those in which the benzyl grouping is substituted in the 2,6-positions by chlorine and/or fluorine atoms.

Preferred compounds are those of formula I wherein $R_1$ represents an alkyl group of 1-6 carbon atoms, for example methyl, ethyl or propyl; $R_2$ represents an optionally substituted alkyl group of 1-6 carbon atoms, for example methyl, ethyl or isopropyl, or a phenyl or benzyl group; $R_3$ represents a hydrogen atom or an optionally substituted alkyl group of 1-6 carbon atoms, for example methyl, hydroxymethyl, chloromethyl, ethyl or isopropyl, or $R_2$ and $R_3$ together represent a polymethylene group of up to 6 carbon atoms, for example tetramethylene or pentamethylene; and $R_4$ represents a 2,6-dihalobenzyl group, e.g. 2,6-dichlorobenzyl or 2-chloro-6-fluorobenzyl.

A particularly preferred example of which is 4-(2,6-dichlorobenzyloxymethyl)-2,2-dimethyl-4-ethyl-1,3-dioxolane.

It will be appreciated that the compounds of the invention may exhibit geometrical and/or optical isomerism. The individual isomers and mixtures thereof are included within the scope of the invention.

The invention includes also a process for the preparation of compounds of formula I which comprises reacting a compound of formula:

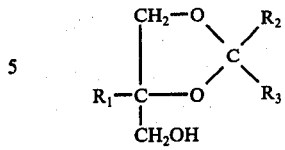

with a strong base and a compound of formula:

wherein Hal represents a halogen suitably chlorine or bromine, atom. The strong base is suitably an alkali metal hydride, for example sodium hydride. The reaction is conveniently carried out in an organic solvent, for example an aromatic hydrocarbon solvent such as toluene.

As mentioned above the compounds of the invention are of interest as herbicides and the invention includes therefore herbicidal compositions comprising a 2,6-dihalobenzyl ether of formula I together with a carrier and/or a surface-active agent. The herbicidal activity of the compounds of the invention is exhibited particularly in pre-emergence application against grass species. However, the compounds show an unexpectedly low activity against wheat and may be used as selective herbicides against grass weeds, e.g. blackgrass, in that crop. The invention includes therefore a method of combating weeds in crops at a locus which comprises applying to the locus a selectively herbicidal amount of a 2,6-dihalobenzyl ether of formula I.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

The surface-active agent may be an emulsifying agent or a dispersing agent or a wetting agent; it may be non-ionic or ionic.

Any of the carrier materials or surface-active agents usually applied in formulating pesticides may be used in the compositions of the invention and suitable examples of these are to be found, for example, in U.K. patent specification No. 1,293,546.

The compositions of the invention may be formulated as wettable powders, dusts, granules, solutions, emulsifiable concentrates, emulsions, suspension concentrates or aerosols. Wettable powders are usually compounded to contain 25, 50 or 75% w of toxicant and usually contain, in addition to solid carrier, 3-10% w of a dispersing agent and, where necessary, 0-10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½-10% w of toxicant. Granules are usually prepared to have a size between 10 and 100 BS mesh (1.676-0.152 mm), and may be manufactured by agglomeration or impregnation techniques. Generally, granules will contain ½-25% w toxicant and 0-10% w of additives such as stabilisers, slow release modifiers and binding agents. Emulsifiable concentrates usually contain, in addition to the solvent and, when necessary, co-solvent, 10-50% w/v toxicant, 2-20% w/v emulsifiers and 0–20% w/v of appropriate additives such as stabilisers, penetrants and corrosion inhibitors. Suspension concentrates are compounded so as to obtain a stable, non-sedimenting, flowable product and usually contain 10–75% w toxicant, 0.5–15% w of dispersing agents, 0.1–10% w of suspending agents such as protective colloids and thixotropic agents, 0–10% w of appropriate additives such as defoamers, corrosion inhibitors, stabilisers, penetrants and stickers, and as carrier, water or an organic liquid in which the toxicant is substantially insoluble; certain organic solids or in-organic salts may be dissolved in the carrier to assist in preventing sedimentation or as anti-freeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick "mayonnaise"-like consistency.

The compositions of the invention may also contain other ingredients, for example, other compounds possessing pesticidal, especially insecticidal acaricidal, herbicidal or fungicidal properties.

The invention is further illustrated in the following examples.

EXAMPLE 1

4-(2,6-Dichlorobenzyloxymethyl)-2,2-dimethyl-4-ethyl-1,3dioxolane

A solution of 2,2-dimethyl-4-hydroxymethyl-1,3-dioxolane (32.0g) in toluene (25 ml) was added slowly to a stirred suspension of sodium hydride (9.6g of 50% dispersion in oil) in toluene (25 ml). After the addition the mixture was heated under reflux for 2 hours. 2,6-Dichlorobenzyl chloride (39.1g) in toluene (100 ml) was then added dropwise and the mixture heated under reflux for a further 4 hours. The cooled mixture was washed with water ($\times 3$) and dried and the solvent was removed under reduced pressure. The residual oil was distilled in vacuo to give the desired product b.p. 156°–162° C at 1.5 mm Hg.

Analysis
Calculated for $C_{15}H_{20}O_3Cl_2$: C, 56.4; H, 6.3; Cl, 22.3%.
Found: C, 56.7; H, 6.7; Cl, 27.3%.

EXAMPLES 2 to 23

Following procedures similar to that of Example 1 further compounds were prepared, whose physical characteristics and analyses are set out in Table 1.

TABLE 1

| Example | Compound | m.p. ° C. b.p. ° C/mmHg or refractive index | Analysis | %C | %H | %Cl |
|---|---|---|---|---|---|---|
| 2 | 4-(2,6-dichlorobenzyloxymethyl)-2,2,4-trimethyl-1,3-dioxolane | 141–6/1.7 | Calculated for $C_{14}H_{18}O_3Cl_2$: Found: | 55.1 55.8 | 5.9 6.2 | 23.3 22.1 |
| 3 | 4-(2,6-dichlorobenzyloxymethyl)-4-methyl-2-spirocyclohexane-1,3-dioxolane | $n_D^{22}$1.5250 | Calculated for $C_{17}H_{22}O_3Cl_2$: Found: | 59.2 59.0 | 6.4 6.5 | 20.6 21.9 |
| 4 | 4-(2,6-dichlorobenzyloxymethyl)-4-methyl-2-spirocyclopentane-1,3-dioxolane | $n_D^{22}$1.5270 | Calculated for $C_{16}H_{20}O_3Cl_2$: Found: | 58.1 57.8 | 6.1 6.2 | 21.4 22.6 |
| 5 | 4-(2,6-dichlorobenzyloxymethyl)-4-ethyl-2-spirocyclohexane-1,3-dioxolane | $n_D^{23}$1.5246 | Calculated for $C_{18}H_{24}O_3Cl_2$: Found: | 60.1 60.1 | 6.7 6.6 | 19.7 20.8 |
| 6 | 4-(2,6-dichlorobenzyloxymethyl)-4-ethyl-2-spirocyclopentane-1,3-dioxolane | $n_D^{23}$1.5230 | Calculated for $C_{17}H_{22}O_3Cl_2$: Found: | 59.1 59.0 | 6.4 6.4 | 20.6 21.3 |
| 7 | 4-(2,6-dichlorobenzyloxymethyl)-2,4-diethyl-2-phenyl-1,3-dioxolane | m.p. 85 | Calculated for $C_{21}H_{24}O_3Cl_2$: Found: | 63.8 63.2 | 6.1 6.2 | 18.0 18.8 |
| 8 | 4-(2,6-dichlorobenzyloxymethyl)-2,4-diethyl-2-methyl-1,3-dioxolane | $n_D^{23}$1.5098 | Calculated for $C_{16}H_{22}O_3Cl_2$: Found: | 57.6 58.0 | 6.6 6.8 | 21.3 22.7 |
| 9 | 4-(2,6-dichlorobenzyloxymethyl)-4-ethyl-2,2-di-isopropyl-1,3-dioxolane | $n_D^{23}$1.5094 | Calculated for $C_{19}H_{26}O_3Cl_2$: Found: | 60.8 60.2 | 7.5 7.6 | 18.9 20.5 |
| 10 | 2-benzyl-4-(2,6-dichlorobenzyloxymethyl)-4-ethyl-2-methyl-1,3-dioxolane | $n_D^{23}$1.5443 | Calculated for $C_{21}H_{24}O_3Cl_2$: Found: | 63.8 64.5 | 6.1 6.2 | 18.0 19.6 |
| 11 | 4-(2,6-dichlorobenzyloxymethyl)-2,4-diethyl 1,3-dioxolane | $n_D^{23}$1.5118 | Calculated for $C_{15}H_{20}O_3Cl_2$: Found: | 56.4 56.9 | 6.3 6.5 | 22.2 22.2 |
| 12 | 4-(2,6-dichlorobenzyloxymethyl)-2,2,4-triethyl-1,3-dioxolane | $n_D^{23}$1.5090 | Calculated for $C_{17}H_{24}O_3Cl_2$: Found: | 58.8 58.4 | 7.0 7.1 | 20.4 22.7 |
| 13 | 4-(2,6-dichlorobenzyloxymethyl)-4-ethyl-2-isopropyl-1,3-dioxolane | $n_D^{20}$1.5119 | Calculated for $C_{16}H_{22}O_3Cl_2$: Found: | 57.7 58.2 | 6.7 6.9 | 21.2 22.9 |
| 14 | 4-(2,6-dichlorobenzyloxymethyl)-4-ethyl-2-hydroxymethyl-2-methyl-1,3-dioxolane | $n_D^{20}$1.5132 | Calculated for $C_{15}H_{20}O_4Cl_2$: Found: | 53.6 54.0 | 6.0 6.1 | 21.2 21.6 |
| 15 | 4-(2-chloro-6-fluorobenzyloxymethyl)-4-ethyl-2,2-dimethyl-1,3-dioxolane | $n_D^{21}$ 1.5102 | Calculated for $C_{15}H_{20}O_3ClF$: Found: | 59.5 59.4 | 6.7 6.6 | 11.7 11.4 |
| 16 | 4-(2-chloro-6-fluorobenzyloxymethyl)-2,2,4-trimethyl-1,3-dioxolane | $n_D^{21}$ 1.5109 | Calculated for $C_{14}H_{18}O_3ClF$: Found: | 58.2 57.8 | 6.3 6.4 | 12.3 13.4 |
| 17 | 4-(2,6-dichlorobenzyloxymethyl)-2,2-dimethyl 4-n-propyl-1,3-dioxolane | 140–3/2 mm | Calculated for $C_{16}H_{22}O_3Cl_2$: Found: | 58.0 58.9 | 6.6 6.8 | 21.3 22.0 |
| 18 | 4-(2,6-dichlorobenzyloxymethyl)-4-n-propyl-2-spirocyclohexane-1,3-dioxolane | $n_D^{20}$ 1.5216 | Calculated for $C_{19}H_{26}O_3Cl_2$: Found: | 61.3 63.3 | 7.0 7.6 | 19.0 18.8 |
| 19 | 4-(2,6-dichlorobenzyloxymethyl)-4-n-propyl- | | Calculated for $C_{16}H_{21}O_3Cl_3$: | 52.0 | 5.7 | 28.7 |

TABLE 1-continued

| Example | Compound | m.p. °C. b.p. °C/mmHg or refractive index | Analysis | | % C | % H | % Cl |
|---|---|---|---|---|---|---|---|
| 20 | 2-chloromethyl-2-methyl-1,3-dioxolane 4-(2,6-dichlorobenzyloxymethyl)-2,4-dimethyl-1,3-dioxolane | 168/0.1 mm | Found : Calculated for $C_{13}H_{16}O_3Cl_2$: | | 54.2 53.6 | 6.0 5.5 | 28.7 24.4 |
| 21 | 4-(2,6-difluorobenzyloxymethyl)-2,2-dimethyl-4-ethyl-1,3-dioxolane | 140/1.0 mm | Found : Calculated for $C_{15}H_{20}O_3F_2$ : | | 53.3 62.9 | 5.4 7.0 | 24.8 13.3 |
| 22 | 4-(2,6-difluorobenzyloxymethyl)-2,2,4-tri-methyl-1,3-dioxolane | 130–132/2.0 mm 125/3.0 mm | Found : Calculated for $C_{14}H_{18}O_3F_2$ : Found : | | 62.5 61.7 61.4 | 6.9 6.7 6.7 | 13.4 14.0 13.8 |

EXAMPLE 23 Herbicidal Activity

To evaluate their herbicidal activity, the compounds of the invention were tested using as a representative range of plants:—maize, Zea mays (Mz); rice, Oryza sativa (R); barnyard grass, Echinchloa crusgalli (BG); pea, Pisum sativum (P); linseed, Linum usitatissium (L); mustard, Sinapis alba (M); and sugar beet, Beta vulgaris (SB).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test, viz. soil drench and foliar spray tests. In the soil drench tests the soil in which seedling plants of the above species were growing, was drenched with a liquid formulation containing a compound of the invention, and in the foliar spray tests the seedling plants were sprayed with such a formulation.

The soil used in the tests was a steam-sterilised, modified John Innes Compost mixture in which half the peat, by loose bulk, had been replaced by vermiculite.

The formulations used in the tests were prepared by diluting with water solutions of the compounds, in acetone containing 0.4% by weight of an alkylphenol-/ethylene oxide concentrate available under the trade name Triton X-155. In the soil spray and foliar spray tests the acetone solutions were diluted with an equal volume of water and the resulting formulations applied at two dosage levels corresponding to 10 and 1 kilograms of active material per hectare respectively in a volume equivalent to 400 liters per hectare. In the soil drench tests one volume of the acetone solution was diluted to 155 volumes with water and the resulting formulation applied at one dosage level equivalent to 10 kilograms of active material per hectare in a volume equivalent to approximately 3,000 liters per hectare.

In the pre-emergence tests untreated sown soil and in the post-emergence tests untreated soil bearing seedling plants were used as controls.

The herbicidal effects of the compounds were assessed visually 7 days after spraying the foliage and drenching the soil and 11 days after spraying the soil, and were recorded on a 0–9 scale. A rating 0 indicates no effect on the treated plants, a rating 2 indicates a reduction in fresh weight of stem and leaf of the plants of approximately 25%, a rating 5 indicates a reduction of approximately 55%, a rating 9 indicates a reduction of 95% etc.

The results of the tests are set out in Table 2.

TABLE 2

| Example | Compound | DOSAGE Kg/ha | POST-EMERGENCE | | | | | | | | | | | | | | PRE-EMERGENCE | | | | | |
|---|---|---|---|---|---|---|---|---|---|---|---|---|---|---|---|---|---|---|---|---|---|---|
| | | | SOIL DRENCH | | | | | | FOLIAR SPRAY | | | | | | | SOIL DRENCH | | | | | | |
| | | | MZ | R | EG | P | L | M | SB | MZ | R | BG | P | L | M | SB | MZ | R | G | P | L | M | SB |
| 2 | 4-(2,6-di-chlorobenzyl-oxymethyl)-2,2,4-tri-methyl-1,3-dioxolane | 10 1 | 7 | 4 | 6 | 0 | 0 | 1 | 0 | 4 0 | 3 0 | 7 4 | 2 1 | 8 1 | 7 1 | 9 0 | 9 5 | 9 9 | 9 9 | 9 8 | 7 2 | 6 1 | 4 0 |
| 1 | 4-(2,6-di-chlorobenzyl-oxymethyl)-2,2-dimethyl-4-ethyl-1,3-dioxolane | 10 1 | 8 | 1 | 8 | 0 | 0 | 0 | 0 | 7 4 | 2 0 | 9 8 | 4 1 | 8 1 | 6 1 | 5 0 | 9 6 | 9 9 | 9 9 | 9 8 | 7 3 | 6 3 | 3 0 |
| 4 | 4-(2,6-di-chlorobenzyl-oxymethyl)-4-methyl-2-spirocyclo-hexane-1,3-dioxolane | 10 1 | 4 | 3 | 7 | 0 | 0 | 0 | 0 | 6 1 | 0 0 | 8 7 | 3 1 | 7 3 | 5 1 | 7 5 | 9 6 | 9 7 | 9 9 | 3 1 | 2 0 | 1 0 | 5 0 |
| 5 | 4-(2,6-di-chlorobenzyl-oxymethyl)-4-methyl-2-spirocyclo-pentane-1,3-dioxolane | 10 1 | 4 | 3 | 8 | 0 | 0 | 0 | 6 | 3 0 | 0 0 | 8 6 | 2 1 | 6 2 | 5 4 | 7 2 | 9 1 | 9 6 | 9 9 | 3 1 | 5 1 | 5 0 | 6 0 |
| 16 | 4-(2-chloro-6-fluoroben-zylmeth-yl)-4-ethyl- | 10 | 6 | 5 | 7 | 4 | 5 | 2 | 7 | 6 | 0 | 7 | 4 | 6 | 0 | 1 | 9 | 9 | 9 | 9 | 6 | 4 | 3 |

TABLE 2-continued

| Example | COMPOUND | DOSAGE Kg/ha | POST-EMERGENCE SOIL DRENCH | | | | | | | FOLIAR SPRAY | | | | | | | PRE-EMERGENCE SOIL DRENCH | | | | | | |
|---|---|---|---|---|---|---|---|---|---|---|---|---|---|---|---|---|---|---|---|---|---|---|
| | | | MZ | R | EG | P | L | M | SB | MZ | R | BG | P | L | M | SB | MZ | R | G | P | L | M | SB |
| | 2,2-dimethyl-1,3-dioxolane | 1 | | | | | | | | 4 | 0 | 5 | 3 | 4 | 0 | 0 | 6 | 9 | 9 | 9 | 5 | 2 | 0 |
| 17 | 4-(2-chloro-6-fluorobenzyloxymethyl)-4-methyl-2,2-dimethyl-1,3-dioxolane | 10 | 9 | 8 | 8 | 9 | 2 | 2 | 5 | 6 | 2 | 6 | 4 | 7 | 2 | 5 | 9 | 9 | 9 | 8 | 5 | 2 | 5 |
| | | 1 | | | | | | | | 3 | 0 | 4 | 2 | 0 | 0 | 0 | 2 | 7 | 9 | 5 | 1 | 0 | 0 |

EXAMPLE 24

COMPARATIVE TESTS

In these tests the herbicidal activity of 4-(2,6-dichlorobenzyloxymethyl)-2,2-dimethyl-4-ethyl-1,2-dioxolane (A) was compared with that of 4-benzyloxymethyl-2,2-dimethyl-4-ethyl-1,3-dioxolane (B) which is known from U.K. specification No. 1,293,546.

Seeds of the test species (wheat and blackgrass) was sown in a modified John Innes Compost mixture in which half the peat, by loose bulk, had been replaced by vermiculite. The sown soil was then watered and sprayed with solutions of the test compound in 1:1 v/v acetone/water containing 0.2% w of an alkylphenol-/ethylene oxide condensate available under the trade name Triton X-155 at seven different dosage levels in the range 0.04–4.0 kg/ha. The herbicidal effects of the compound were assessed visually 2-3 weeks after spraying, and the results used to calculate the dosage levels necessary to produce a 10%, and 50% 90% reduction in the fresh weight of stem and leaf of the test plants compared with untreated controls.

The calculated dosage levels are set out in Table 3, from which it will be seen that the compound (A) is considerably less active than compound (B) against wheat. At the same time (A) is very active against blackgrass and may therefore be used to combat this weed in wheat crops.

TABLE 3

| TEST SPECIES | DOSAGE LEVELS | | | | | |
|---|---|---|---|---|---|---|
| | (A) | | | (B) | | |
| | 10 | 50 | 90% | 10 | 50 | 90% |
| Wheat | 3.27 | >4.00 | >4.00 | <0.10 | 0.31 | 1.03 |
| Blackgrass | 0.04 | 0.07 | 0.19 | — | — | — |

What we claim is:

1. A method of combatting weeds in crops at a locus which comprises applying to the locus a selectively herbicidal amount of a 2,6-dihalobenzyl ether of the formula

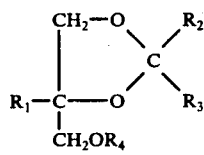

wherein $R_1$ and $R_2$ each is methyl or ethyl; $R_3$ is hydrogen, methyl or ethyl and $R_4$ is 2,6-dichlorobenzyl, 2-chloro-6-fluoro-benzyl or 2,6-difluorobenzyl.

2. A method according to claim 1 wherein the 2,6-dihalobenzyl ether has a structure in which $R_1$ is ethyl; $R_2$ and $R_3$ each is methyl and $R_4$ is 2,6-dichlorobenzyl.

3. A method according to claim 1 wherein the 2,6-dihalobenzyl ether has structure in which $R_1$, $R_2$ and $R_3$ each is methyl and $R_4$ is 2,6-dichlorobenzyl.

4. A method according to claim 1 wherein the 2,6-dihalobenzyl ether has a structure in which $R_1$ is ethyl; $R_2$ and $R_3$ each is methyl and $R_4$ is 2-chloro-6-fluorobenzyl.

5. A method according to claim 1 wherein $R_1$, $R_2$ and $R_3$ are each methyl and $R_4$ is 2,6-difluorobenzyl.

6. A method according to claim 1 wherein $R_1$ and $R_2$ are each ethyl; $R_3$ is methyl and $R_4$ is 2,6-dichlorobenzyl.

7. A method according to claim 1 wherein the weeds are grasses and the crop is wheat.

8. A herbicidal composition comprising as active ingredient a 2,6-dihalobenzyl ether as described in claim 1 and at least one carrier or surface active agent.